US00PP36816P2

(12) United States Plant Patent
Holtmaat

(10) Patent No.: US PP36,816 P2
(45) Date of Patent: Jul. 8, 2025

(54) ***RUDBECKIA* PLANT NAMED 'RUDBSUN303'**

(50) Latin Name: *Rudbeckia hirta*
Varietal Denomination: RUDBSUN303

(71) Applicant: Henricus Maria Joseph Holtmaat, Zuidwolde (NL)

(72) Inventor: Henricus Maria Joseph Holtmaat, Zuidwolde (NL)

(73) Assignee: NOVA PERENNE BV, Zuidwolde (NL)

( * ) Notice: Subject to any disclaimer, the term of this patent is extended or adjusted under 35 U.S.C. 154(b) by 0 days.

(21) Appl. No.: 19/037,040

(22) Filed: Jan. 24, 2025

(51) Int. Cl.
*A01H 5/02* (2018.01)
*A01H 6/14* (2018.01)

(52) U.S. Cl.
USPC ..... Plt./474
CPC ..... *A01H 6/14* (2018.05)

(58) Field of Classification Search
USPC ..... Plt./474
CPC ..... A01H 6/14; A01H 5/02
See application file for complete search history.

*Primary Examiner* — Keith O. Robinson
(74) *Attorney, Agent, or Firm* — Penny J. Aguirre

(57) ABSTRACT

A new cultivar of *Rudbeckia* plant named 'RUDBSUN303' that is characterized by its short plant height, its compact plant habit, its inflorescences with bi-colored ray florets with red towards the centers and yellow towards the distal end, its blooming that commences early in the season, and its floriferous blooming habit.

2 Drawing Sheets

Botanical classification: *Rudbeckia hirta.*
Variety denomination: 'RUDBSUN303'.

CROSS-REFERENCE TO RELATED APPLICATIONS

This application claims priority to European Community Plant Variety Office (CPVO) Plant Breeder's Rights Application No. 2023/1794 filed on Jul. 31, 2024, under 35 U.S.C. 119(f), the entire contents of which is incorporated by reference herein. The Applicant received the information for the Plant breeders' rights application directly from the Inventor. This application is also co-pending with U.S. Plant Patent Applications filed for plants derived from the same breeding program that are entitled *Rudbeckia* Plant Named 'RUDBCHR650' (U.S. Plant patent application Ser. No. 19/037,008 and *Rudbeckia* Plant Named 'RUDBDIV658' (U.S. Plant patent application Ser. No. 19/037,027).

BACKGROUND OF THE INVENTION

The present invention relates to a new and distinct cultivar of *Rudbeckia hirta* and will hereafter by referred to by its cultivar name, 'RUDBSUN303'. The new cultivar is an herbaceous perennial grown for use as a landscape plant.

'RUDBSUN303' was selected in July of 2019 by the Inventor from amongst seedlings in a trial field in Zuidwolde, Netherlands that had been planted with seed derived from open pollination of numerous unpatented and unnamed proprietary plants from the Inventor's breeding program. The exact parentage is therefore unknown.

Asexual propagation of the new cultivar was first accomplished under the direction of the Inventor by tissue culture using meristematic tissue in Heerhugowaard, The Netherlands in October of 2021. Asexual propagation by tissue culture has determined that the characteristics of the new cultivar are stable and are reproduced true to type in successive generations.

SUMMARY OF THE INVENTION

The following traits have been repeatedly observed and represent the characteristics of the new cultivar. These attributes in combination distinguish 'RUDBSUN303' as a unique cultivar of *Rudbeckia.*

1. 'RUDBSUN303' exhibits a short plant height.
2. 'RUDBSUN303' exhibits a compact plant habit.
3. 'RUDBSUN303' exhibits inflorescences with bi-colored ray florets with red towards the centers and yellow towards the distal end.
4. 'RUDBSUN303' exhibits blooming that commences early in the season.
5. 'RUDBSUN303' exhibits a floriferous blooming habit.

'RUDBSUN303' can be compared to the *Rudbeckia* cultivars 'RUDHT25' (U.S. Plant Pat. No. 30,728) and 'RUDKI096' (not patented). 'RUDHT25' is similar to 'RUDBSUN303' in foliage coloration and in having inflorescences with bi-colored ray florets. 'RUDHT25' differs from 'RUDBSUN303' in having a taller plant height, ray florets that contain a larger portion that is yellow in color, and in commencing bloom later in the season. 'RUDKI096' is similar to 'RUDBSUN303' in having inflorescences with bi-colored ray florets that are similar in color. 'RUDKI096' differs from 'RUDBSUN303' in having a taller plant height, a less floriferous blooming habit, and in commencing bloom much later in the season.

'RUDBSUN303' can also be compared to the co-pending cultivars of *Rudbeckia*; 'RUDBCHR650' and 'RUDBDIV658'. Both are similar to 'RUDBSUN303' in having short plant heights and in commencing bloom early in the season. Both 'RUDBCHR650' and 'RUDBDIV658' differ from 'RUDBSUN303' in having inflorescences that lack bi-colored ray florets.

BRIEF DESCRIPTION OF THE DRAWINGS

The accompanying color photographs illustrate the overall appearance and distinct characteristics of the new *Rudbeckia*. The photographs were taken of a 3-month-old plant of 'RUDBSUN303' as grown outdoors in a 19-cm container in Zuidwolde, The Netherlands.

The photograph in FIG. 1 is a side view of 'RUDBSUN303' in bloom.

Figure 1:
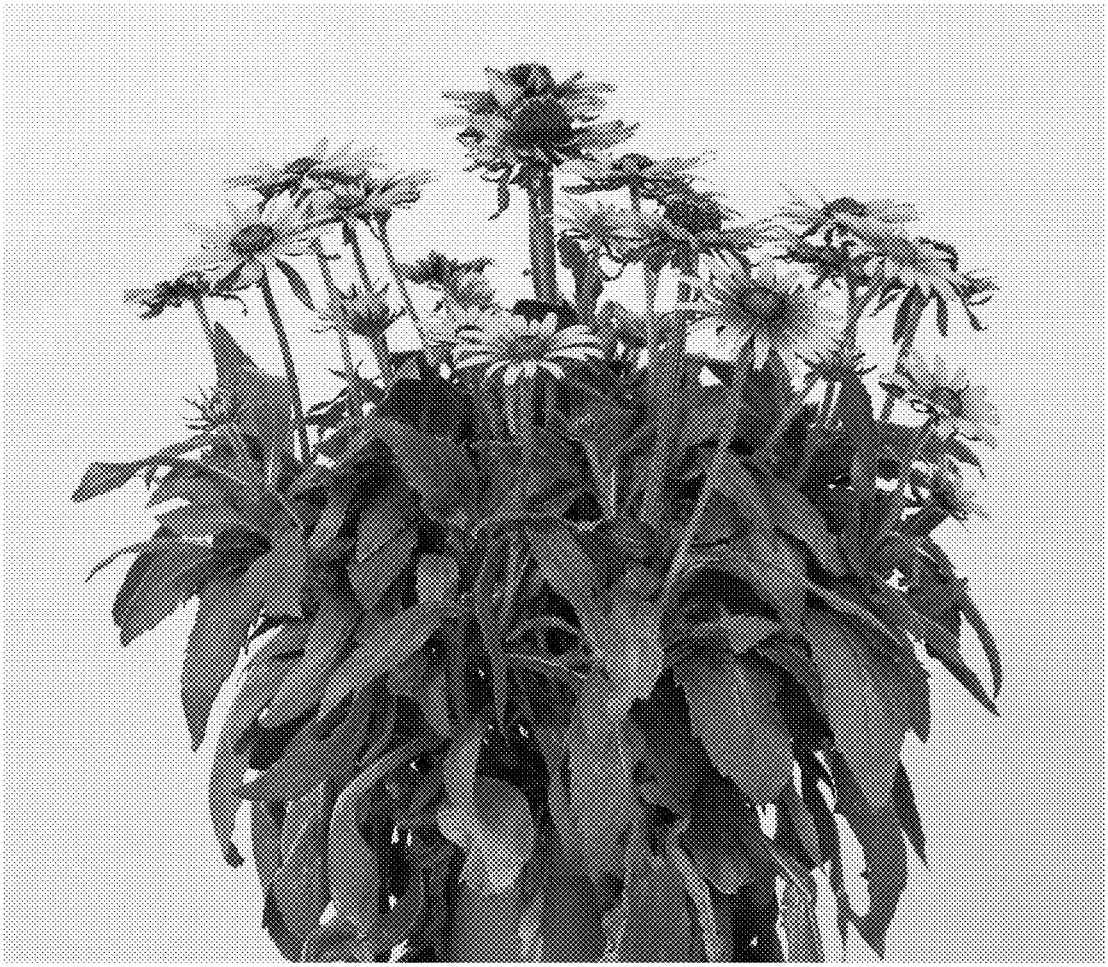
Figure 2:
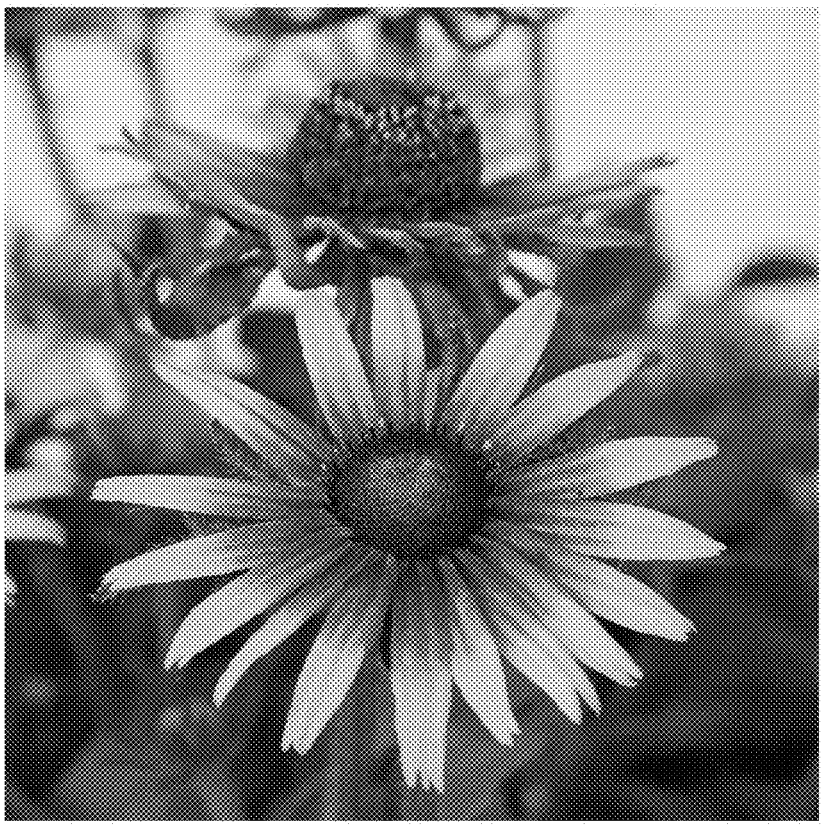

The photograph in FIG. 2 provides a close-up view of an inflorescence of 'RUDBSUN303'.

Figure 3:
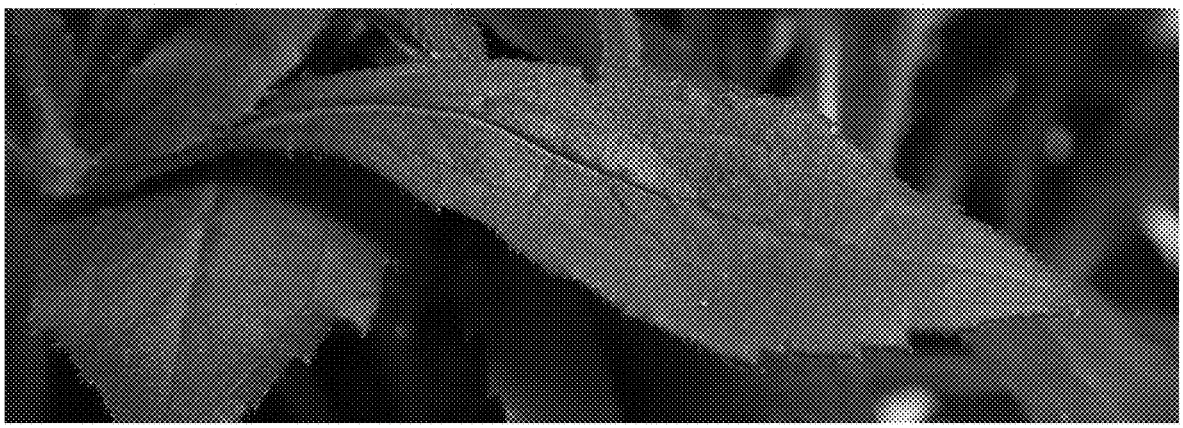

The photograph in FIG. 3 provides a close-up view of a leaf of 'RUDBSUN303'.

The colors in the photographs are as close as possible with the photographic and printing technology utilized and the color values cited in the detailed botanical description accurately describe the colors of the new *Rudbeckia*.

BOTANICAL DESCRIPTION OF THE PLANT

The following is a detailed description of 3-month-old plants of 'RUDBSUN303' as grown outdoors in 19-cm containers in Zuidwolde, The Netherlands. The phenotype of the new cultivar may vary with variations in environmental, climatic, and cultural conditions, as it has not been tested under all possible environmental conditions. The color determination is in accordance with The 2015 Colour Chart of The Royal Horticultural Society, London, England, except where general color terms of ordinary dictionary significance are used.

General description:

*Blooming period*.—June to July in The Netherlands.

*Plant type*.—Perennial.

*Plant habit*.—Broadly upright, compact.

*Plant shape*.—Flattened globular to broadly obovate.

*Height and spread*.—Average of 35 cm in height from soil level to top of foliar plane and 44 cm in height from soil level to top of floral plane, 51.5 cm in diameter as a 3-month-old plant as grown in a container.

*Hardiness*.—At least in U.S.D.A. Zones 4 to 10.

*Diseases and pests*.—No susceptibility or resistance to diseases or pests has been observed.

*Root description*.—Fine and fibrous.

*Propagation*.—Tissue culture.

*Root development*.—An average of 2 weeks for root initiation with a young rooted plant produced in an average of 4 weeks.

*Growth rate and vigor*.—Moderate vigorous.

Stem description:

*Shape*.—Moderately angled, 5-sided.

*Stem color*.—Young stems; 144A, mature stems; 144A, tinged with 183B.

*Stem size*.—An average of 5 mm in diameter and an average of 13.5 cm in length.

*Stem surface*.—Moderately glossy and densely covered with strigose hairs an average of 2 mm in length and N155A in color.

*Stem number*.—Average of 14 main stems, 3 lateral branches per main stem.

*Internode length*.—An average of 2.5 cm in length.

*Stem aspect*.—Main stems; average of 30° to vertical, lateral branches; average of 20° to main stems.

*Branching*.—Freely branching from base with lateral stems.

Foliage description:

*Leaf shape*.—Oblanceolate to narrow obovate.

*Leaf division*.—Simple.

*Leaf base*.—Long cuneate.

*Leaf apex*.—Acute.

*Leaf venation*.—Pinnate, color upper surface 144A, color lower surface 146C.

*Leaf margins*.—Coarsely serrate, coarsely slightly undulate.

*Leaf attachment*.—Petiolate.

*Leaf arrangement*.—Alternate.

*Leaf size*.—Average of 18.6 cm in length and 5.2 cm in width.

*Leaf color*.—Young upper surface; 137B, young lower surface; 143A, mature upper surface; NN137B, mature lower surface; 137B.

*Leaf surface*.—Upper surface very slightly glossy, lower surface slightly glossy, both surfaces rough to the touch, densely pubescent with short strigose hairs; an average of 1.5 mm in length and 156D in color.

*Petioles*.—Average of 4.5 mm in length, strong, flattened, average diameter at widest point 9 mm and at narrowest point 4 mm, upper surface color; 145C, margins 145A, lower surface color; 145B, both surfaces slightly glossy and densely covered with strigose hairs; an average of 1.5 mm in length and 156D in color.

Flower description:

*Type*.—Terminal capitulum, consisting of ray florets and disc florets.

*Capitulum number*.—5 per stem, up to 65 per plant.

*Lastingness of inflorescence*.—Average of 2 weeks, persistent.

*Capitulum size*.—Matures to about 3.4 cm in height and 9.9 cm in diameter, disc size is an average of 2.9 cm in diameter.

*Fragrance*.—None.

*Involucral bracts* (*phyllaries*).—Cuneate base, acute apex, narrow oblong in shape, entire margins, average of 35 arranged in 3 rows, rotate, moderately curved upward, 3 cm in length and 2.5 mm in width, color; upper surface when fully open NN137B, lower surface when fully open 138A, both surfaces matte and densely covered with strigose hairs; an average of 2 mm in length and 187A in color, margins are moderately to densely covered with strigose hairs; 1.5 mm in length and 156D in color.

*Receptacle*.—Broad ovate in shape, an average of 1.3 cm in height and diameter, 157B in color, receptacle spines; single bract is placed besides each individual disc floret, spirally placed on disc, soft, flattened and moderately pubescent, 8 mm in length, 1.5 mm in diameter, oblanceolate in shape, acute apex, narrow cuneate base, matte surfaces, color; apex is 145B and 145C, very top 187A, mid-section is 157A, narrowly margined 187A, base is 157A, narrowly margined 187A.

*Buds*.—Shape; broad ovate, immature ray florets pointed upward and slightly curled inwards, 2.3 cm in length, width; excluding involucral bracts 2.1 cm, including involucral bracts 5.1 cm, surfaces are matte and densely covered with strigose hairs, average length of hairs on immature ray florets 1 mm, average length of hairs on involucral bracts; 0.1 cm, color on involucral bracts; NN155D, and immature ray florets; 154D, hairs on immature ray florets adpressed.

*Peduncle*.—Strong, straight on top of main flowering stem, average of 16.2 cm in length and 4.5 mm in diameter, color; 143A and 144A, surface moderately glossy and densely covered with short strigose hairs; an average of 2 mm in length and 156D in color.

*Ray florets*.—Average of 20, rotate around the disc, narrow oblong to lanceolate in shape, average of 4.1 cm in length and 9.5 mm in width, emarginate to praemorse apex, cuneate base, entire margins, both surfaces are glabrous and velvety, densely covered with very short adpressed hairs, 0.5 mm in length and 14B in color, color; when opening upper surface 14A to 14B, lower half 17A, when opening lower surface 13A to 13B, when fully open upper and lower surface 17B to 17C, lower half 169C, base 175A, upper surface changing to 17A, tinged 167A, lower half a blend of 166A and 187A, lower surface changing to 13A to 13B, tinged 144A.

*Disc flowers*.—Arranged spirally on a conical receptacle, 1,250 per inflorescence, 25 rows, lower 92.5% fused into tube, tubular, upright, about 9 mm in length and 4.5 mm in width, tubular, upper 7.5% free, free lobes have entire margins, apices of free lobes acute and curled backwards, both surfaces glabrous and slightly glossy, color; when opening upper and lower surface 200A, lower half 155C, when fully open upper and lower surface 203A, tinged 200A, lower half 155C.

Reproductive organs:

*Gynoecium*.—Pistil; 1, 6.5 mm in length, style; 4.5 mm in length, stigma; cleft, decurrent, 203A in color, 5 mm in diameter, 157A to 157D in color, ovary; N155C in color.

*Androecium*.—Stamens; 5, filaments; 3 mm in length, 155A in color, anther; narrow oblong in shape, 2.5 mm in length, 0.5 mm in width, 203A in color, pollen; moderate in quantity and 17A in color.

*Fruit/seed*.—None observed.

It is claimed:

1. A new and distinct cultivar of *Rudbeckia* plant named 'RUDBSUN303' substantially as herein illustrated and described.

* * * * *